United States Patent
Egas et al.

(10) Patent No.: US 6,752,030 B2
(45) Date of Patent: Jun. 22, 2004

(54) SLEEVE WITH GUIDANCE RING

(75) Inventors: Rudd Egas, Berkel en Rodenrijs (NL); Jose Blach-Romay, ZA Rotterdam (NL)

(73) Assignee: DQS International B.V., Rotterdam (NL)

(*) Notice: Subject to any disclaimer, the term of this patent is extended or adjusted under 35 U.S.C. 154(b) by 235 days.

(21) Appl. No.: 09/902,970

(22) Filed: Jul. 11, 2001

(65) Prior Publication Data

US 2002/0033057 A1 Mar. 21, 2002

Related U.S. Application Data

(60) Provisional application No. 60/220,404, filed on Jul. 24, 2000.

(51) Int. Cl.[7] .................................................. G01N 1/00
(52) U.S. Cl. ..................................................... 73/864.74
(58) Field of Search .......................... 73/863.86, 864.21, 73/864.22, 864.23, 864.24, 864.74

(56) References Cited

U.S. PATENT DOCUMENTS

| 3,991,627 A | * 11/1976 | Laird et al. ............... 73/864.23 |
| 5,604,320 A | 2/1997 | Boyd |
| 5,925,833 A | 7/1999 | Peterson |
| 5,948,998 A | 9/1999 | Witte et al. |
| 6,105,441 A | 8/2000 | Conner et al. |
| 6,112,604 A | 9/2000 | Peterson |

* cited by examiner

*Primary Examiner*—Robert Raevis
(74) *Attorney, Agent, or Firm*—Synnestvedt, Lechner & Woodbridge, LLP; Richard C. Woodbridge, Esq.; Roy Rosser

(57) ABSTRACT

The invention relates to a device for safely aligning the mouth of a sample container with the sample needle of a liquid sampling device. A guidance ring holds the mouth of the sample container in position under the sample needle. The sample container and guidance ring slide inside the sleeve guide to allow the mouth of the sample container to slide up the sleeve guide so that the sample needle can pierce the septum of the sample container. The sample needle is recessed in the sleeve guide so that the likelihood of needle sticks is greatly reduced.

2 Claims, 3 Drawing Sheets

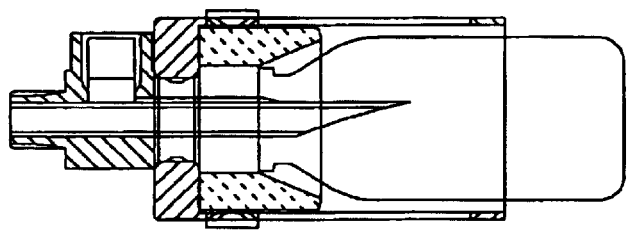
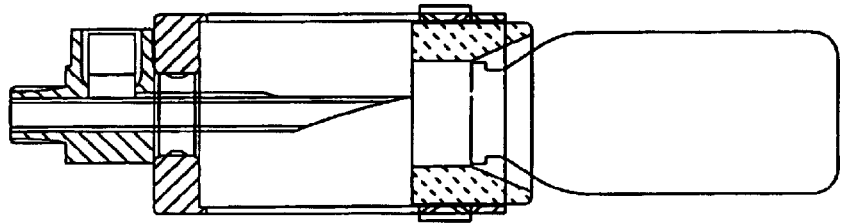
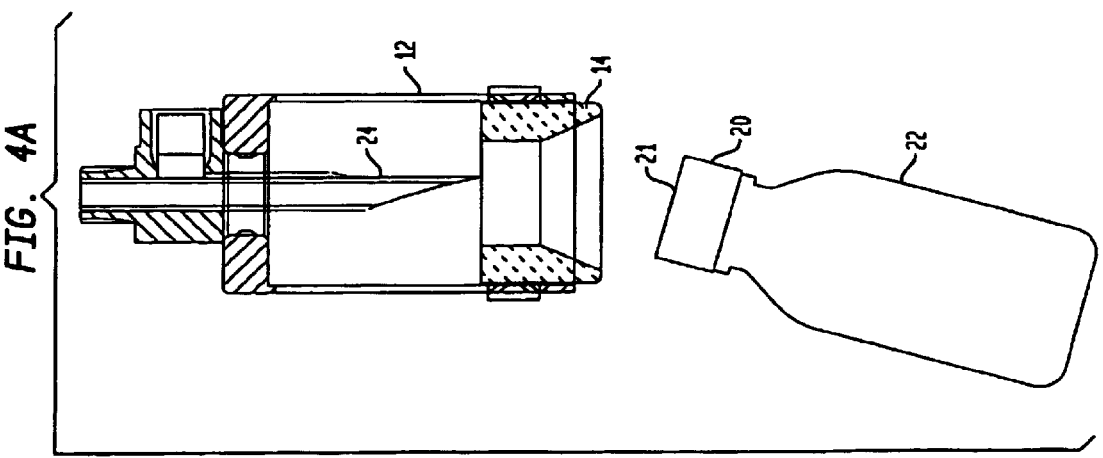

SLEEVE WITH GUIDANCE RING

CROSS REFERENCE TO RELATED APPLCATIONS

This application claims the priority of U.S. Provisional Application Ser. No. 60/220404 entitled "Sleeve with Guidance Ring" filed on Jul. 24, 2000 the entire contents and substance of which are hereby incorporated in total by reference.

BACKROUND OF THE INVENTION

1. Field of the Invention

The invention relates to a device for safely aligning the mouth of a sample container with the sample needle of a liquid sampling device.

2. Description of Related Art

The septum at the mouth of liquid sample containers must be precisely aligned with the sample needle to ensure that the septum is directly under the needle when the needle is inserted into the container. Typically, sample containers have a fair degree of dimensional tolerance and various manufacturers make containers, which hold the same volume, with different external dimensions. This tolerance makes precise alignment of the septum with the sample needle difficult and increases the likelihood of needle sticks.

U.S. Pat. No. 4,887,472 issued on Dec. 19, 1989 to Jansen discloses a closed loop sampler, which comprises a hood with an integrally formed sampling and venting needle. One end of the hood is thread mounted to a valve; the other end is mounted to a sliding sleeve, which receives a sample container sealed with a septum. The lower end of the hood is itself sealed with a septum. Samples are taken by sliding the sleeve with sample container upward towards the valve causing the two needles to penetrate the first septum which seals the hood, and then the septum of the sample container. The valve is then opened, and a sample is drawn. Upon completion of the sample draw, the sleeve is slid downward withdrawing the needles from the septum of the sample container as well as the septum of the hood. Sample needles may be cleaned before the next sample by circulating a wash fluid into the sealed area around the needles defined by the lower septum of the hood and the needles to flush away any traces of the old sample before a new sample is taken. One drawback to this invention is that should one or both of the sample needle or flush needle become clogged, it is necessary to replace the entire hood mechanism because of the integral formation of the sample and flush needles with the hood.

U.S. Pat. No. 5,604,320 issued on Feb. 18, 1997 to Boyd discloses a sampling apparatus with a ring insert and a shroud to guide the sample container. The ring insert of the Boyd patent is made to fit on the outside of the sample container and is removable from both the sample container and the shroud. Therefore each different type of sample container must have a corresponding ring insert. The need for a different ring insert to accommodate differences in sample container external dimensions complicates the task of retrieving a sample. If the proper ring insert is not available then manual alignment must be attempted. Further there is greater likelihood that the ring insert will be lost because the ring insert can be removed from the shroud.

SUMMARY OF THE INVENTION

Briefly described, the invention comprises two parts. First, is a cylindrical sleeve with two diametrically opposed slots cut into the sides and running along the sleeve axis. Second, is a guidance ring, which fits inside the sleeve and slides up and down on two diametrically opposed tabs which fit into the slots on the sleeve. The inside of the guidance ring is sized to accept the mouth of a sample container and the outside of the guidance ring is sized to fit inside the sleeve guide.

To operate the apparatus, the mouth of a sample container is inserted into the guidance ring, and the ring is slid up the sleeve until the sample needle pierces the septum. The guidance ring improves the alignment of the septum with the sample needle and reduces the likelihood of needle sticks because the sample container is held firmly in alignment with the sample needle.

BRIEF DESCRIPTION OF THE DRAWINGS

FIGS. 4A–C show the steps in placing a sample container in place to take a sample.

DETAILED DESCRIPTION OF THE PREFERRED EMBODIMENT

During the course of this description like numbers will be used to identify like elements according to the different views, which illustrate the invention.

Figure 1:
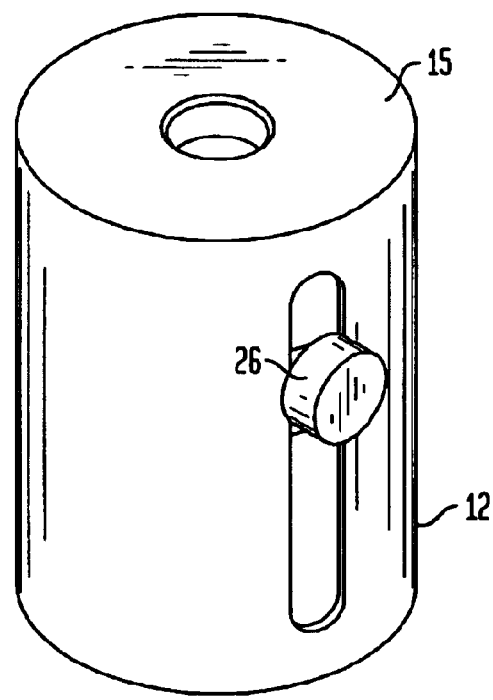
FIG. 1 illustrates the complete apparatus fully assembled according to the preferred embodiment.
Figure 2:
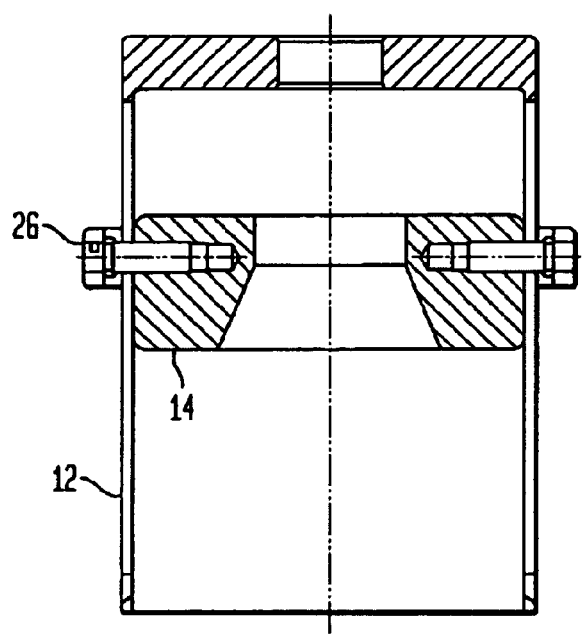
FIG. 2 illustrates a cut away of the complete apparatus fully assembled according to the preferred embodiment.
Figure 3A:
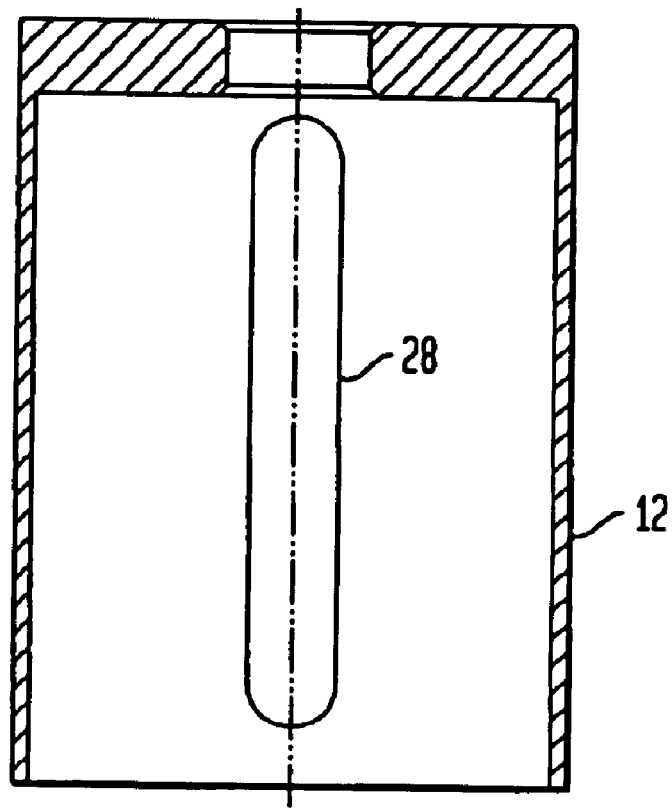
FIG. 3A illustrates a cross section of the sleeve guide.
Figure 3B:
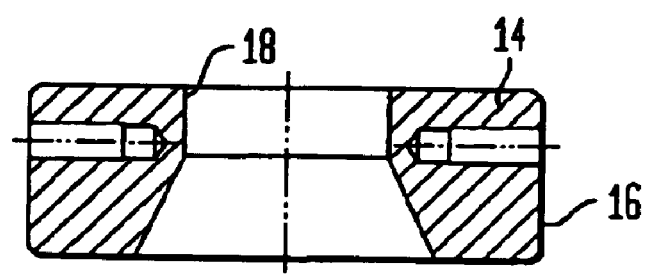
FIG. 3B illustrates cross section of the guidance ring.

The invention 10 as shown in FIGS. 1, 2, 3A and 3B comprises a cylindrical sleeve guide 12 and a sliding guidance ring 14. The top of the sleeve guide 15 is attached to a liquid sampling device so that the sample needles extend into the sleeve guide. The outer diameter 16 of the guidance ring 14 is dimensioned to closely fit inside the sleeve guide 12 so as to slide up and down in the sleeve guide. The inside diameter 18 of the guidance ring 14 is dimensioned so as to accept the mouth of a sample container 20 and is tapered to allow easier placement of the sample container 20. The mouth of the sample container 20 fits securely inside the guidance ring 14 so as to position the septum 21 of the sample container 22 directly below the sampling needle 24. As shown in FIG. 1, the guidance ring 14 is prevented from falling out of the sleeve guide by two tabs 26 located on the outside diameter 16 of the guidance ring 14. The tabs 26 are diametrically opposed around the guidance ring 14 and fit into two corresponding slots 28 running along the axis of the sleeve guide. The tabs 26 and slots 28 allow the guidance ring 14 to slide from one end of the sleeve guide 12 to the other end of the sleeve guide without falling out of the sleeve guide.

Operationally, the sample container 22 is positioned under the sleeve guide 12 as shown in FIG. 4A. The mouth of the sample container 20 is inserted into the guidance ring 14 as shown in FIG. 4B. The guidance ring 14 thus provides the indexing and proper location for the mouth of the sample container 22 relative to the sampling needles 24. The sample container 22 is then slid up so that the sampling needles 24 pierce the septum 21 as shown in FIG. 4C. The process is reversed to remove the container.

The present invention possesses several advantages over the prior art:

First, the external dimensions of sample containers vary from manufacturer to manufacturer for sample containers of the same volume. These variations in container volume are accommodated by the fact that the septum and cap diameters are standard. Thus a septum and cap for a small sample container can be the same size as the septum and cap of a large container and the container will still fit in the guidance ring.

Second, guidance ring 14 remains inside the sleeve guide 12 and is available for use whenever a sample is needed.

Third, guidance ring 14 eliminates the necessity of a ring insert as shown in Boyd thus reducing the likelihood of losing the ring.

Fourth, alignment between the sample container and sample needle is improved because guidance ring 14 both aligns and firmly holds the sample container in position while it is moved into place under the needles.

Fifth, a further improvement is that the likelihood of failing to insert the needle into the septum is greatly reduced thus reducing the possibility of a release of toxic contaminants into the environment.

While the invention has been described with reference to the preferred embodiment thereof, it will be appreciated by those of ordinary skill in the art that modifications can be made to the structure and elements of the invention without departing form the spirit and scope of the invention as a whole.

We claim:

1. An apparatus to align the mouth of a sample container with a sample needle of a sample device, said apparatus comprising:

a sleeve guide comprising a cylinder having a cylinder wall, a first end, a second end, and an inside diameter and a top;

a guidance ring comprising an annulus having an annulus wall, an inside diameter and an outside diameter, said inside diameter of said guidance ring dimensioned to securely hold said mouth of said sample container and said outside diameter of said guidance ring dimensioned to slidably fit inside said sleeve guide; and at least two diametrically opposed tabs attached to said outside diameter of said guidance ring said tabs comprising bolts threaded into holes in said outside diameter of said annulus wall of said guidance ring; and alignment means for aligning said guidance ring in said sleeve guide, said alignment means including at least two diametrically opposed slots cut in said cylinder wall of said sleeve guide, said slots starting at said first end of said sleeve guide and ending at said second end of said sleeve guide, said slots slidably accepting said tabs of said guidance ring so that said guidance ring may slide inside said sleeve guide from said first end of said sleeve guide to said second end of said sleeve guide to move said sample container into contact with said sample needle.

2. The apparatus of claim 1 further comprising:

a mounting means on said top of said sleeve guide whereby said sleeve guide may be attached to said sample device and said sample needle extends into said sleeve guide.

* * * * *